United States Patent
Sawada et al.

(10) Patent No.: US 7,826,980 B2
(45) Date of Patent: Nov. 2, 2010

(54) CUMULATIVE CHEMICAL/PHYSICAL PHENOMENON DETECTING APPARATUS

(75) Inventors: Kazuaki Sawada, Toyohashi (JP); Takeshi Hizawa, Kawasaki (JP); Junichi Matsuo, Toyohashi (JP); Yuki Maruyama, Toyohashi (JP)

(73) Assignee: National University Corporation Toyohashi University of Technology, Aichi (JP)

( * ) Notice: Subject to any disclaimer, the term of this patent is extended or adjusted under 35 U.S.C. 154(b) by 373 days.

(21) Appl. No.: 11/886,130

(22) PCT Filed: Mar. 13, 2006

(86) PCT No.: PCT/JP2006/304868

§ 371 (c)(1),
(2), (4) Date: Apr. 4, 2008

(87) PCT Pub. No.: WO2006/095903

PCT Pub. Date: Sep. 14, 2006

(65) Prior Publication Data

US 2008/0231253 A1 Sep. 25, 2008

(30) Foreign Application Priority Data

Mar. 11, 2005 (JP) .............................. 2005-069501

(51) Int. Cl.
*G01N 27/60* (2006.01)

(52) U.S. Cl. ...................... 702/22; 257/253; 250/208.1; 250/214 R; 422/82.01; 204/400; 204/412

(58) Field of Classification Search ................... 702/22; 257/252, 253, 254, 414; 250/208.1, 214 R; 422/82.01, 68.1, 82.02, 82.03, 83, 98; 204/400, 204/412, 415, 416, 431, 433

See application file for complete search history.

(56) References Cited

U.S. PATENT DOCUMENTS

| 4,974,240 | A | * | 11/1990 | Suzuki et al. | .................. 377/60 |
| 5,247,554 | A | * | 9/1993 | Yamada | ........................ 377/60 |
| 5,656,835 | A | * | 8/1997 | Komobuchi | .................. 257/232 |
| 6,255,678 | B1 | * | 7/2001 | Sawada et al. | ............... 257/253 |
| 7,049,645 | B2 | * | 5/2006 | Sawada et al. | ............... 257/292 |
| 7,098,087 | B2 | * | 8/2006 | Akimoto et al. | ............. 438/151 |
| 7,424,372 | B2 | * | 9/2008 | Mimura et al. | ................. 702/22 |
| 2004/0021177 | A1 | * | 2/2004 | Akimoto et al. | ............. 257/347 |
| 2005/0062093 | A1 | * | 3/2005 | Sawada et al. | ............... 257/316 |
| 2006/0261341 | A1 | * | 11/2006 | Akimoto et al. | ............... 257/66 |
| 2008/0018958 | A1 | * | 1/2008 | Kurokawa | .................... 358/474 |

FOREIGN PATENT DOCUMENTS

| JP | 61-38624 | 8/1986 |
| JP | 4-100384 | 4/1992 |

(Continued)

*Primary Examiner*—Carol S Tsai
(74) *Attorney, Agent, or Firm*—Brian McGuire; Matthew K. Ryan; Frommer Lawrence & Haug LLP

(57) ABSTRACT

A sensitivity of a cumulative chemical/physical phenomenon detecting apparatus is improved. Prior to transferring charges at a sensing section to a floating diffusion section, the charges remaining at the sensing section are removed from the sensing section by a potential barrier formed between the sensing section and a charge injection adjusting section.

8 Claims, 22 Drawing Sheets

FOREIGN PATENT DOCUMENTS

| | | |
|---|---|---|
| JP | 6-14706 | 2/1994 |
| JP | 10-332423 | 12/1998 |
| JP | 10332423 A * | 12/1998 |
| JP | 11/301775 | 7/1999 |
| JP | 2002-98667 | 4/2002 |
| JP | 2002098667 A * | 4/2002 |

* cited by examiner (the vertical axes indicate potential of electron, in which downward direction and upward direction mean higher potential and lower potential, respectively)

output characteristic of the apparatus (the vertical axes indicate potential of electron, in which downward direction and upward direction mean higher potential and lower potential, respectively)

residual charge signal charge interface state (the vertical axes indicate potential of electron, in which downward direction and upward direction mean higher potential and lower potential, respectively)

CUMULATIVE CHEMICAL/PHYSICAL PHENOMENON DETECTING APPARATUS

FIELD OF THE INVENTION

The invention relates to a charge accumulating type chemical and physical phenomenon detecting apparatus (or merely called the apparatus).

BACKGROUND OF THE INVENTION

Typical examples of charge accumulating type chemical and physical phenomenon detecting apparatuses are disclosed in patent document 1 and patent document 2.

FIG. 1 shows an example of using a charge accumulating type chemical and physical phenomenon detecting apparatus for measuring ion concentration.

On a silicon substrate 10, n+ type dope regions 11, 13, and a p type dope region 15 are formed. In the p type dope region 15, a silicon oxide film 19 is deposited as a gate insulation film. On this silicon oxide film 19, two gate electrodes 22 and 24 are provided. Reference numeral 23 in the drawing is a silicon nitride film. On the silicon nitride film 23, a liquid cell 31 is provided, which is filled with an aqueous solution 32 for measuring the ion concentration (pH). Reference numeral 26 is a reference electrode, which is kept at a specific potential.

Those provided in the substrate, that is, the n+ region 11, the gate electrode 22, the gate electrode 24, and the n+ region 13 are respectively connected to terminals ID, ICG, TG, and FD, and a specific potential is applied at a specific timing. As a result, the n+ region 11 of the substrate becomes a charge supply unit 1, the portion corresponding to the gate electrode 22 becomes a charge injection adjusting part 2, the portion corresponding to the silicon nitride film 23 becomes a sensing part 3, the portion corresponding to the gate electrode 24 becomes a barrier part 4, and the n+ type region 13 becomes a floating diffusion part 5.

In the charge accumulating type chemical and physical phenomenon detecting apparatus of the prior art having such configuration, a theoretical operation is shown in FIG. 2.

In standby state S1, an electric charge is accumulated in a floating diffusion part 5. This charge is accumulated by unit detection operation up to the last time. At this time, corresponding to the ion concentration of a solution 32, the potential of a sensing part 3 is changed.

By lowering the potential to be applied to a charge supply unit 1, an electric charge is supplied in the sensing part 3 (step 3). Consequently, by raising the potential of the charge supply unit 1, the charge scooped by a charge injection adjusting part 2 is left over in the sensing part 3 (step 5). At step 7, this residual charge is accumulated in the floating diffusion part 5.

By repeating the unit detection operations at step 1 to step 7, the charge is accumulated in the floating diffusion part 5. As a result, the sensitivity of detection is enhanced as shown in FIG. 3.

Patent document 1: Japanese Patent Application Laid-Open (JP-A) No. 10-332423

Patent document 2: JP-A No. 2002-98667

DISCLOSURE OF THE INVENTION

Problems to be Solved by the Invention

According to the studies by the present inventors, it was difficult to enhance the sensitivity as shown in FIG. 3 by repeating the unit detection operations by using the apparatus shown in FIG. 1.

An actual sensor output characteristic was as shown in FIG. 4A. FIG. 4B shows a theoretical sensor output characteristic. If the flex point of an output curve is not clear as shown in FIG. 4A, accurate measurement is impossible. In other words, sufficient sensitivity is not obtained.

The inventors intensively investigated to find the cause of drop of sensitivity, and found that the sensitivity is lowered because of accumulation of trace charges in the sensing part, regardlessly of chemical or physical phenomenon to be detected.

One of the causes of accumulation of charge in the sensing part lies in a potential bump (barrier) 40 formed between the charge injection adjusting part 2 and the sensing part 3 as shown in FIG. 5. Due to existence of this bump 40, at step 5, the charge not supposed to be accumulated is left over in the sensing part 3, and it is then transferred to the floating diffusion part 5 (see FIG. 6).

A second cause lies in the charge trapped in the interface state of the sensing part 3. The residual charge is also transferred to the floating diffusion part and causes to lower the sensitivity (see FIG. 7).

Means for Solving the Problems

A first aspect of the invention has a configuration as described below.

A charge accumulating type chemical and physical phenomenon detecting apparatus including a removing means for removing the charge remaining in the sensing part due to the potential bump formed between the sensing part and the charge injection adjusting part, from the sensing part.

According to the first aspect of the invention having such configuration, since the charge remaining in the sensing part is removed by the removing means, it is not transferred to the floating diffusion part. Hence, the output characteristic is improved, and the sensitivity is enhanced.

As the removing means, an elimination well is provided consecutively to the sensing part, and the charge remaining in this elimination well may be temporarily put aside. The elimination well can be provided in a simple structure of disposing electrodes, and thus the apparatus is not complicated. Therefore, an inexpensive apparatus can be presented.

An example of this elimination well 50 is shown in FIG. 8.

According to the studies by the inventors, when the potential at the bottom of the elimination well 50 is constant, a new bump 51 is formed, and the charge is not scooped sufficiently due to the bump 51, and the charge is left over in the sensing part (see FIG. 8).

Accordingly, the depth of a potential well of this elimination well is varied. More specifically, as shown in FIG. 9, by lowering the potential of the elimination well 50 and increasing the depth of the well, the charge in the sensing part 3 is sucked into the elimination well 50. At this time, the bump 52 existing in the sensing part 3 disappears when a fringing field is formed by an electric field forming the elimination well 50. As a result, the charge existing in the sensing part 3 can be sucked in.

In this example, by changing the potential in one elimination well, the depth of the potential well of the elimination well is changed, but by forming a new elimination well, too, the residual charge in the sensing part can be sucked in.

The charge sucked in the elimination well is desired to be removed from the elimination well. In an embodiment of the invention, the potential of the charge injection adjusting part is set higher than that of the elimination well, and the charge in the elimination well is distributed into the charge supply unit.

The charge may be trapped in the interface state existing between the silicon substrate corresponding to the sensing part 3 and the silicon oxide film, and it may take a long time until sucked completely in the elimination well or the floating diffusion part. To solve this problem, the position of charge existing in the sensing part is preferred to be separated from the substrate surface. More specifically, by doping an n type impurity in the surface of a p type region for forming the sensing part, the charge existing position can be transferred from the substrate surface to its inside (see FIG. 10).

As a result, trapping of charge of the sensing part 3 in the interface state can be prevented.

DESCRIPTION OF THE REFERENCE NUMERALS

Figure 1:
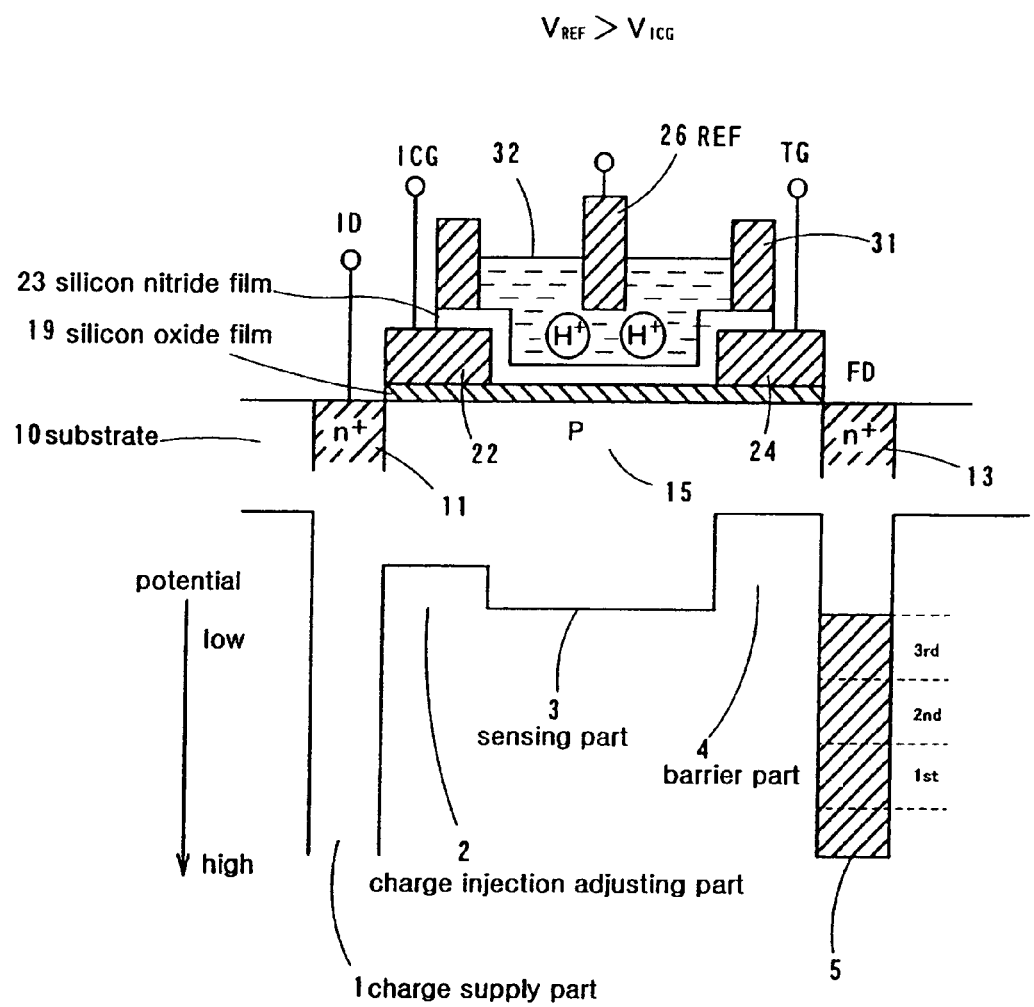
FIG. 1 is a sectional view of a charge accumulating type chemical and physical phenomenon detecting apparatus in a prior art.
Figure 2:
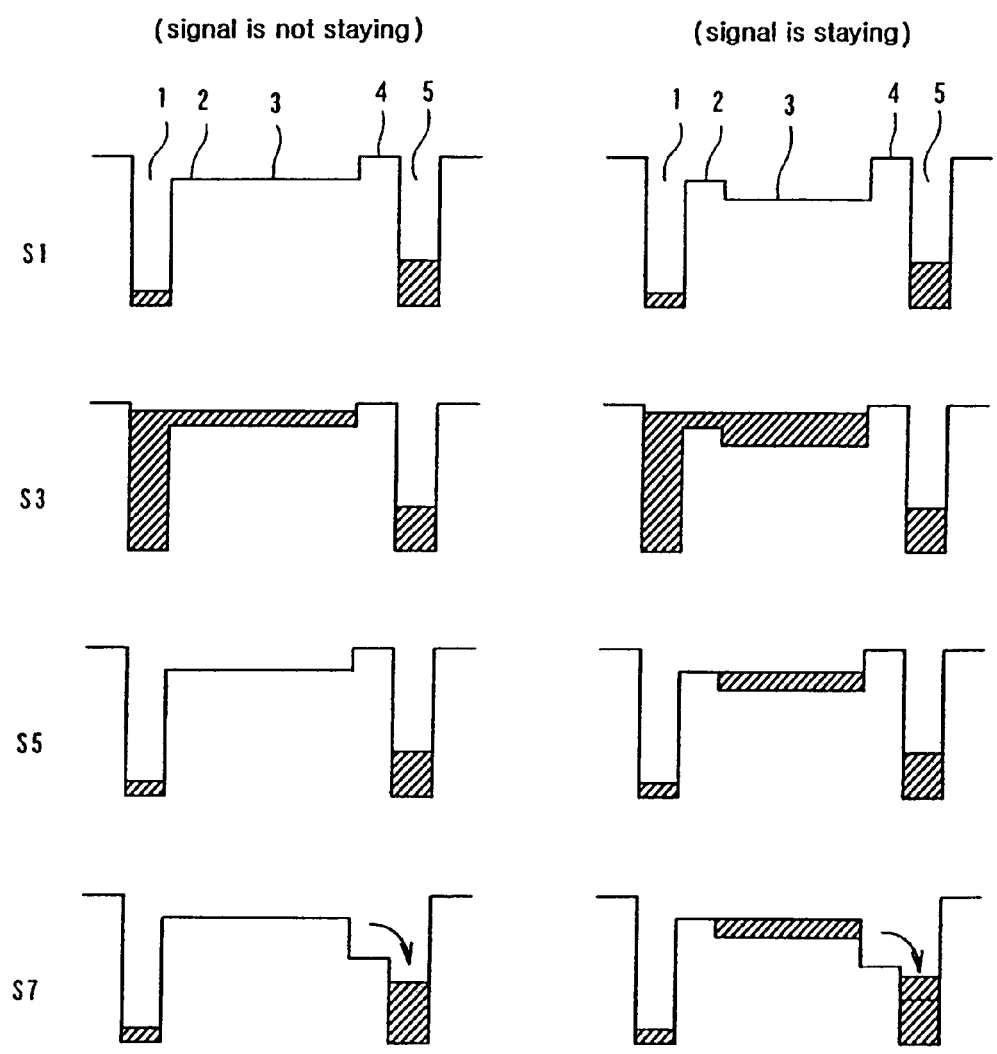
FIG. 2 shows a theoretical operation of the charge accumulating type chemical and physical phenomenon detecting apparatus.
Figure 3:
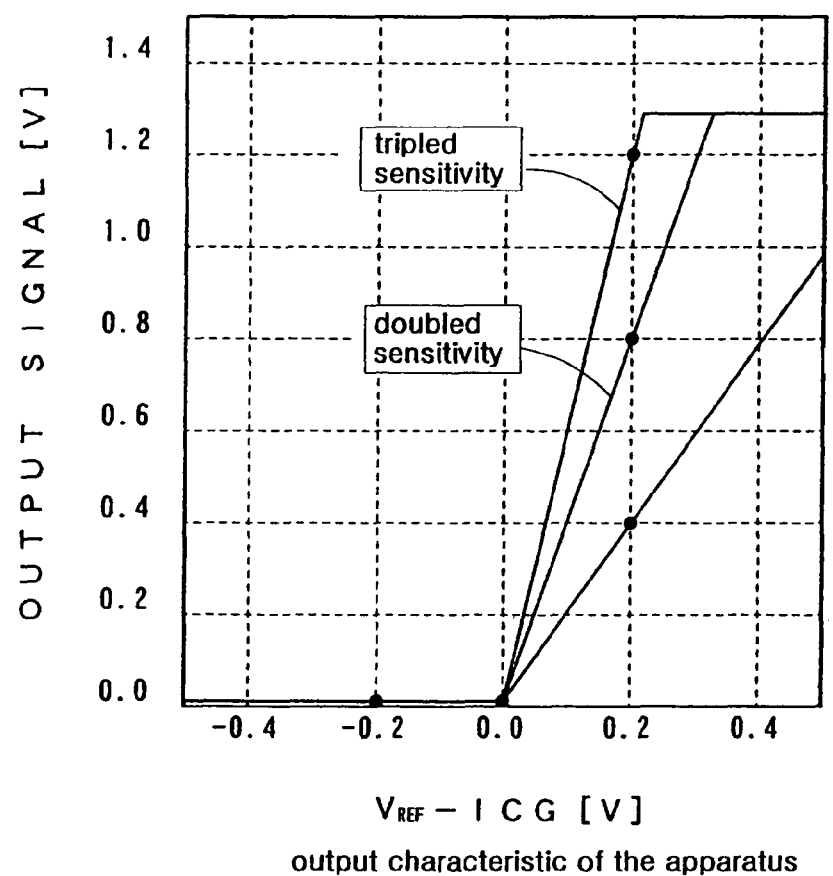
FIG. 3 shows a theoretical output characteristic of the charge accumulating type chemical and physical phenomenon detecting apparatus.
Figure 4:
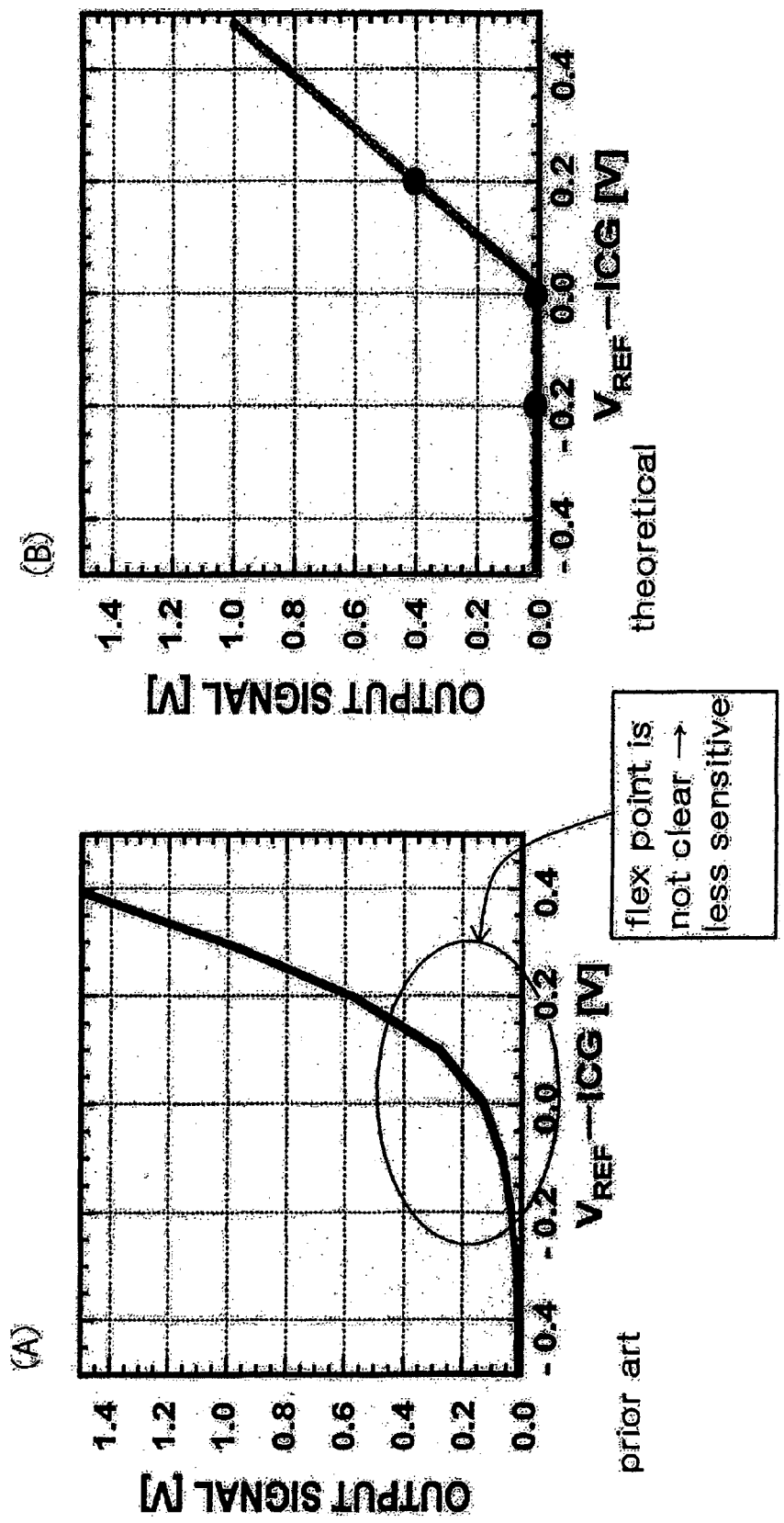
FIG. 4A shows an output characteristic of the charge accumulating type chemical and physical phenomenon detecting apparatus in a prior art.
FIG. 4B shows its theoretical output characteristic.
Figure 5:
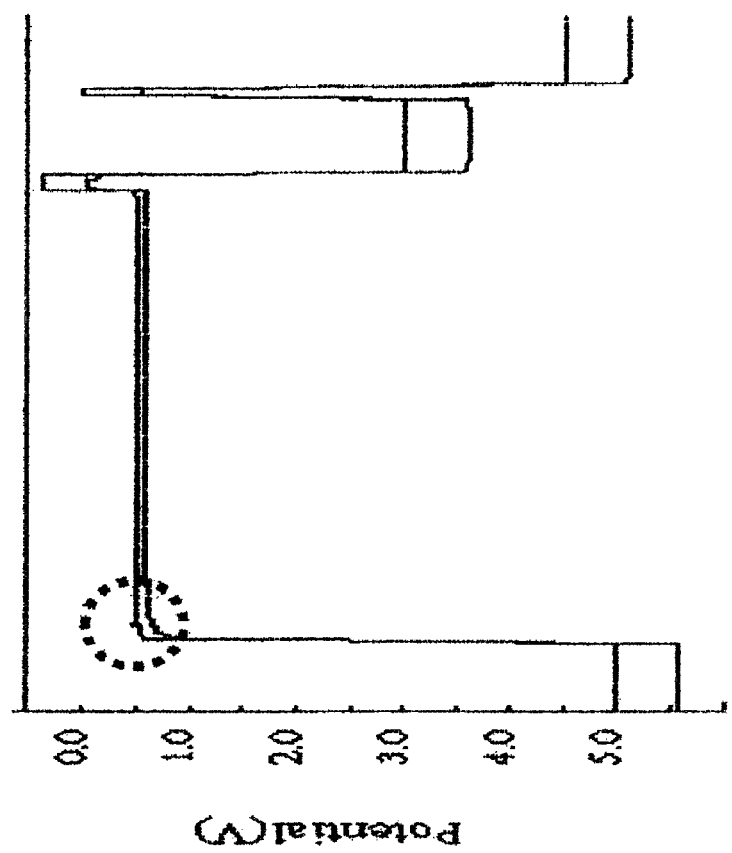
FIG. 5 is an explanatory diagram of a false signal generation mechanism of the charge accumulating type chemical and physical phenomenon detecting apparatus in a prior art.
Figure 5:
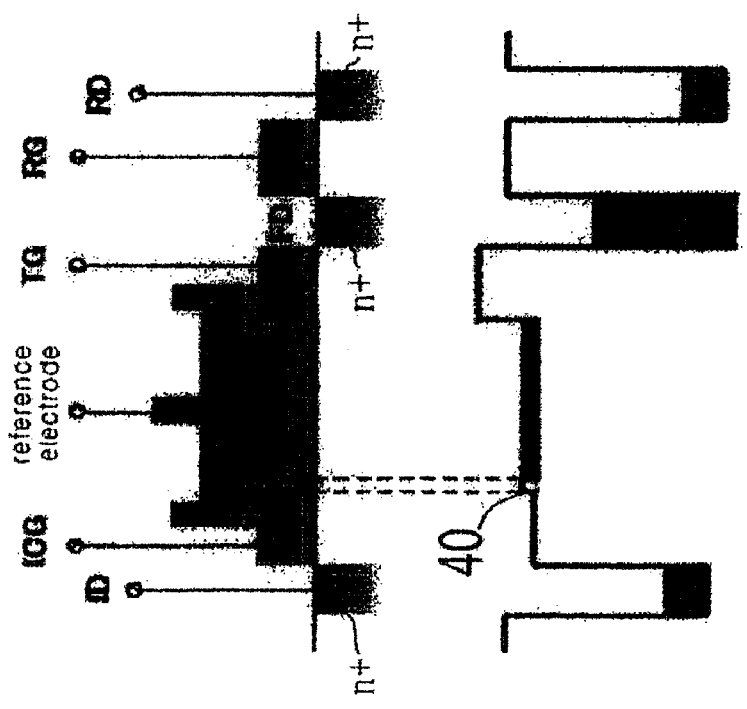
Figure 6:
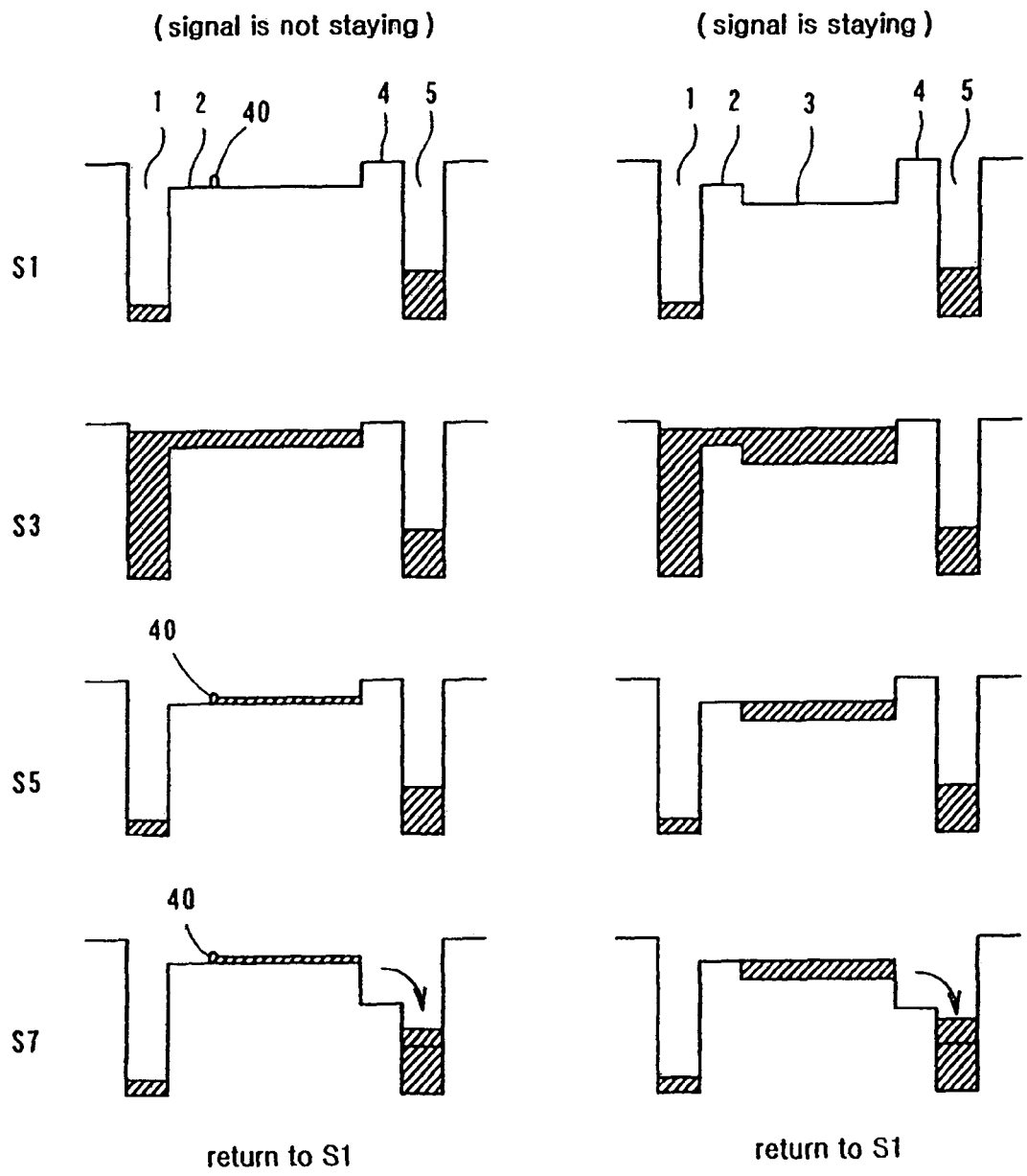
FIG. 6 shows an operation of the charge accumulating type chemical and physical phenomenon detecting apparatus in a prior art in which a charge is remaining in a sensing part.

1 Charge supply unit
2 Charge injection control part
3 Sensing part
4 Barrier
5 Floating diffusion part
10 Substrate
11, 13 n+ region
15 p region
19 Silicon oxide film
22, 24, 62 Electrode
23 Silicon nitride film
26 Reference electrode
32 Aqueous solution
40, 51, 52 Potential bump
50 Elimination well Embodiments An embodiment of the invention is described below.

Figure 11:
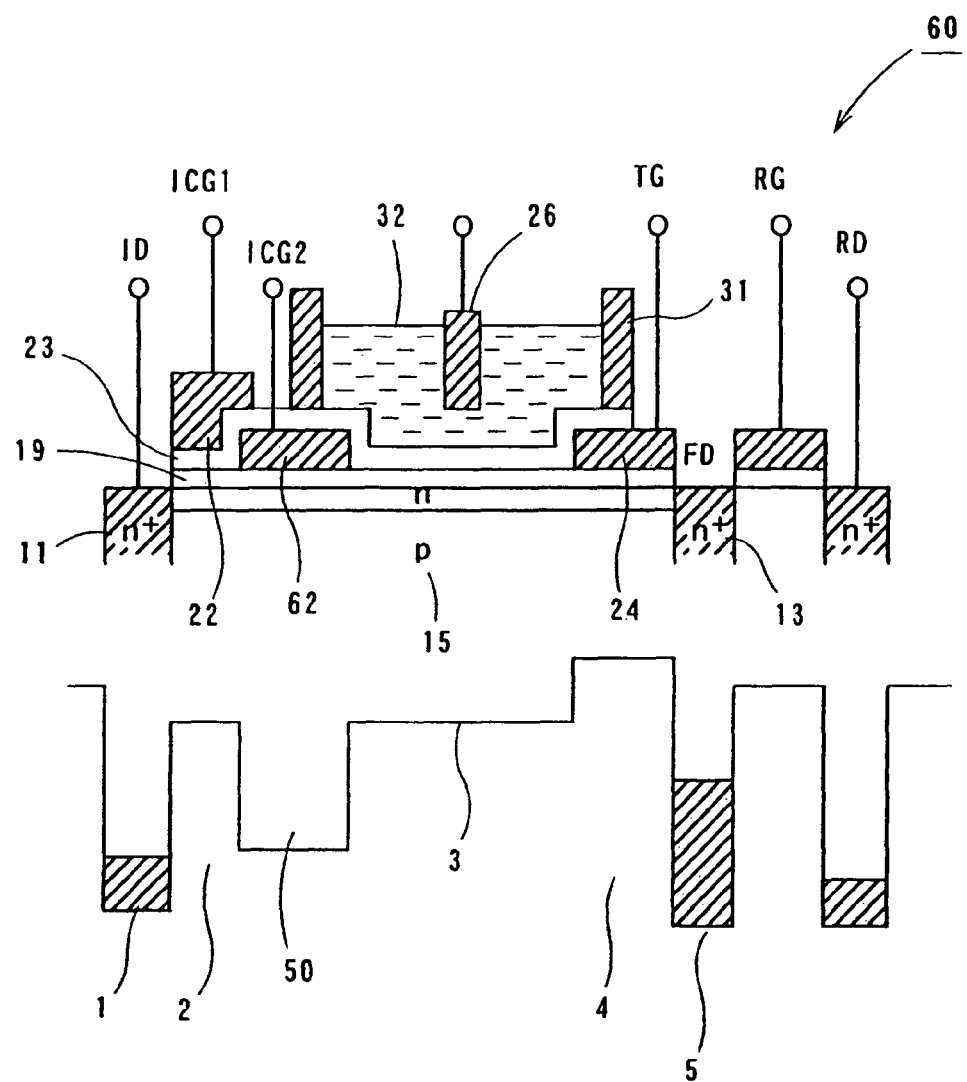
FIG. 11 is a schematic diagram of the charge accumulating type chemical and physical phenomenon detecting apparatus in an embodiment of the invention.

A charge accumulating type chemical and physical phenomenon detecting apparatus 60 of the embodiment is shown in FIG. 11. In FIG. 11, same parts as in FIG. 1 are identified with same reference numerals and explanation is omitted.

The apparatus 60 of the embodiment includes a gate electrode (first charge control electrode) 22 and an elimination electrode (second charge control electrode) 62 formed between a charge supply unit 1 and a sensing part 3. The elimination electrode 62 controls the potential of the elimination well 50. The surface of a p type region 15 is transformed to an n type by polysilicon. As a result, trapping of charge in the surface state of the sensing part 3 is prevented.

Figure 12:
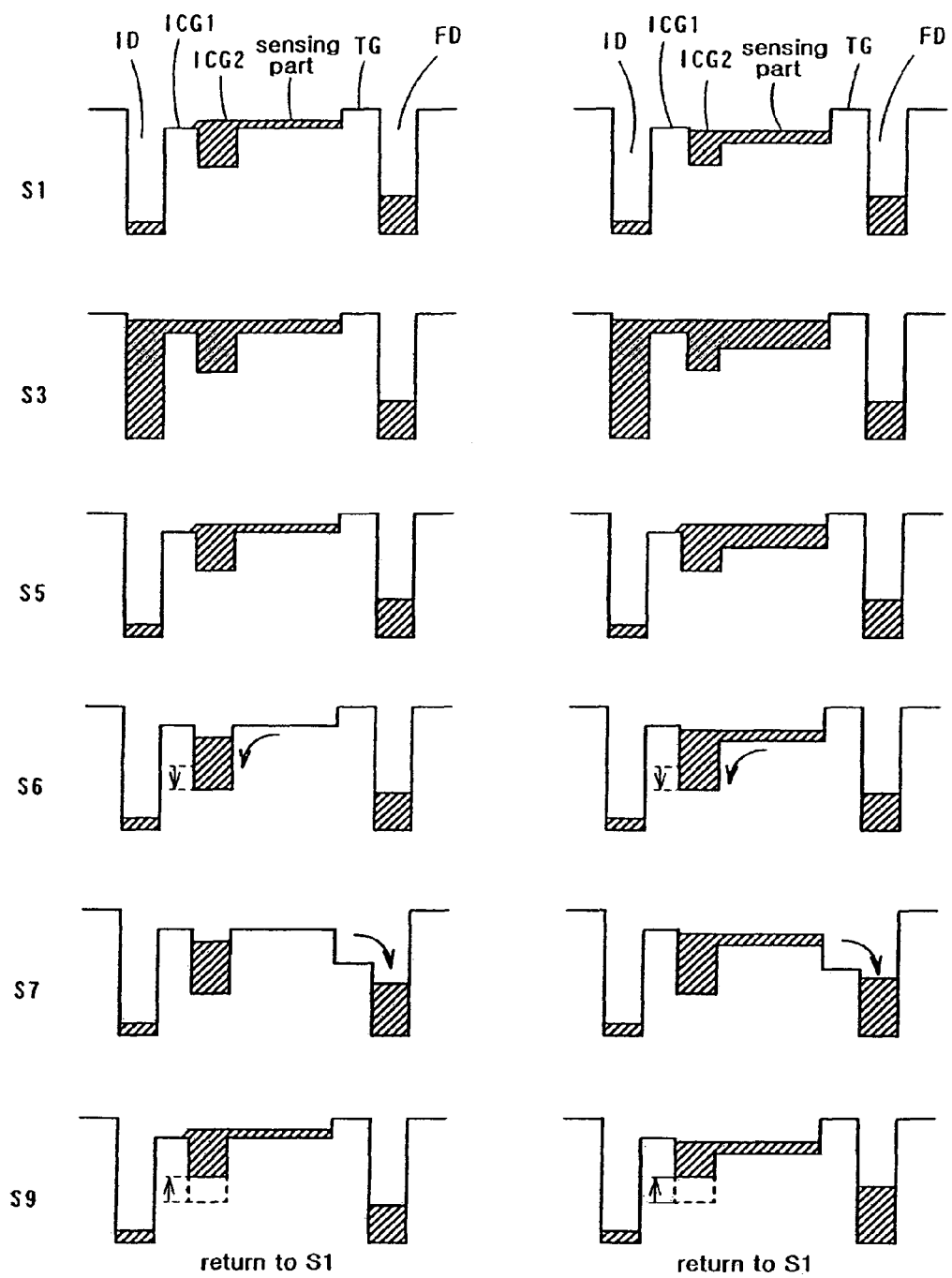
FIG. 12 shows an operation of the charge accumulating type chemical and physical phenomenon detecting apparatus in an embodiment.

Operation of the apparatus of the embodiment is explained with reference to FIG. 12.

Figure 8:
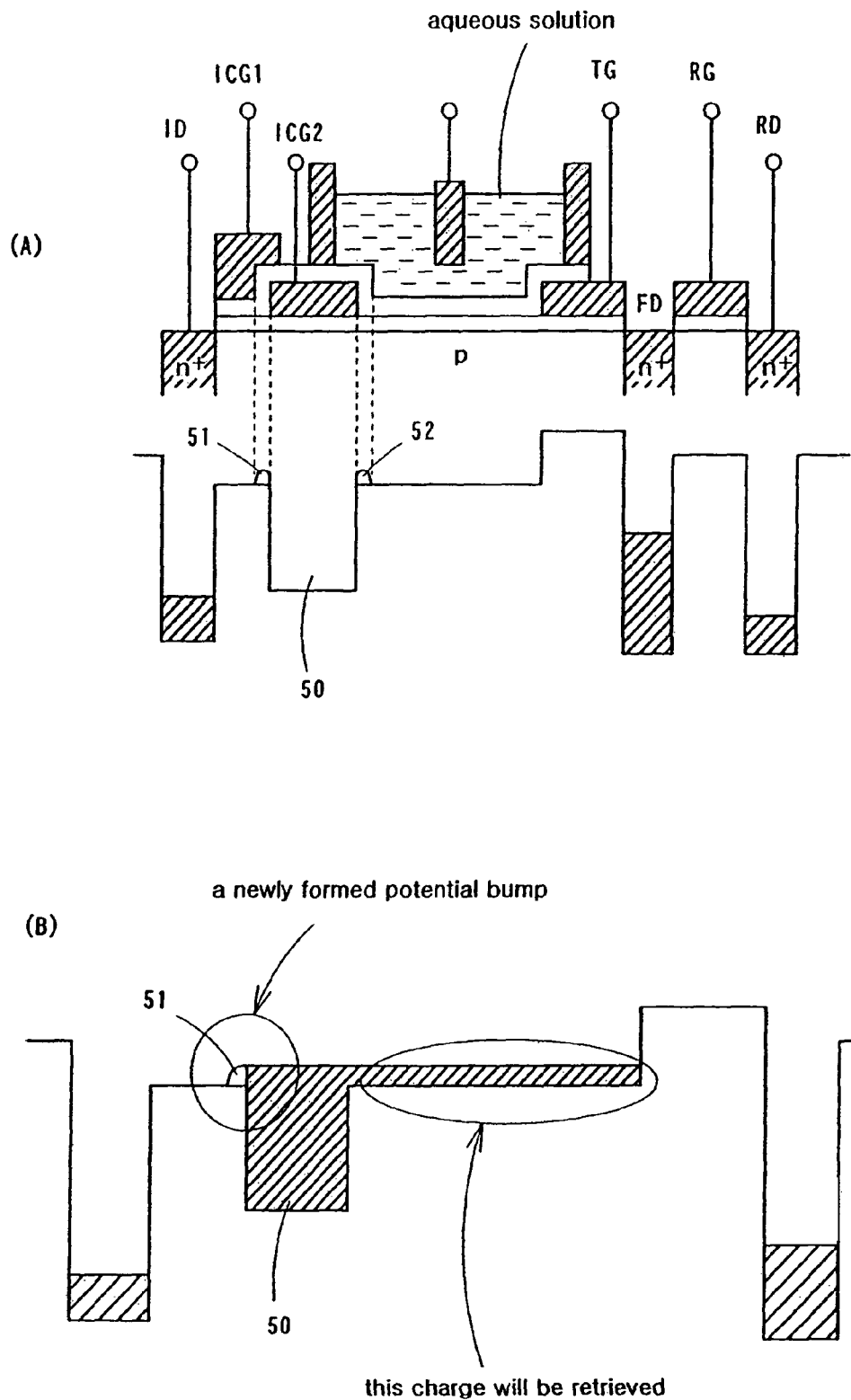
FIG. 8 is a schematic configuration diagram of the charge accumulating type chemical and physical phenomenon detecting apparatus of the present invention.
Figure 9:
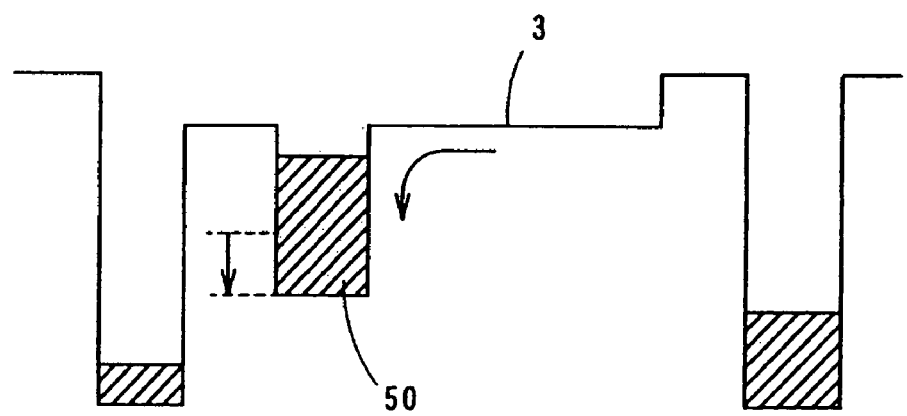
FIG. 9 is a schematic diagram of operation of an elimination well of the charge accumulating type chemical and physical phenomenon detecting apparatus of the invention.
Figure 9:
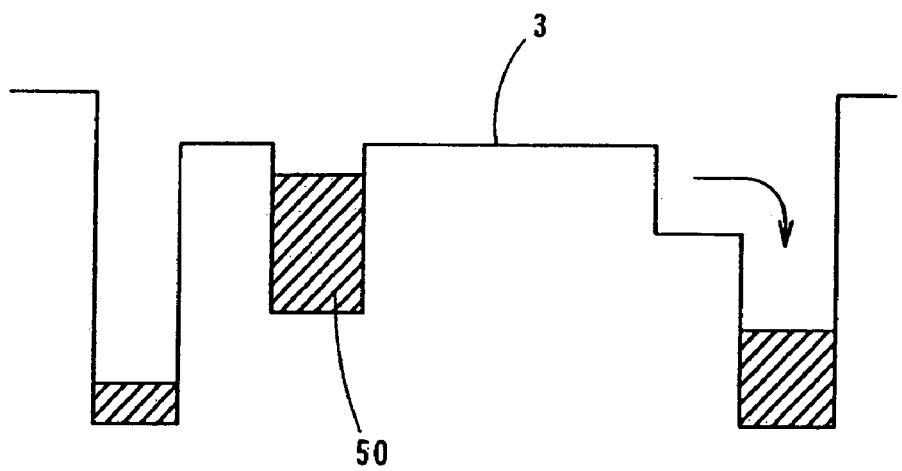
Figure 10:
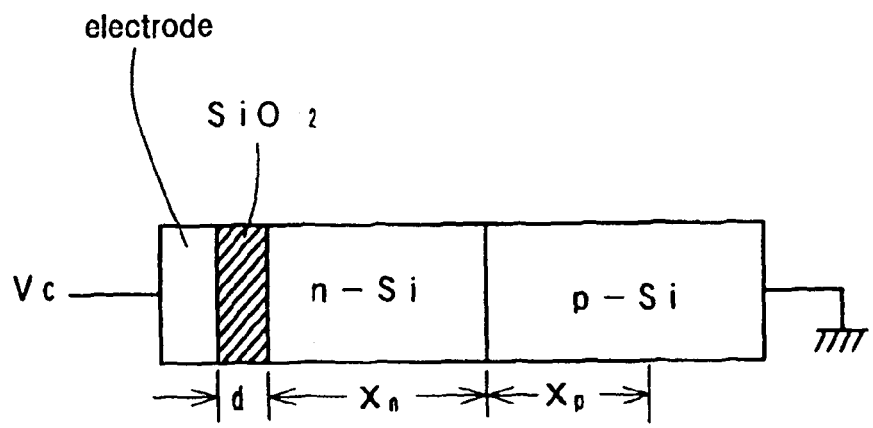
FIG. 10 is a schematic diagram of a state of the substrate surface of the sensing part in the charge accumulating type chemical and physical phenomenon detecting apparatus of the invention.
Figure 10:
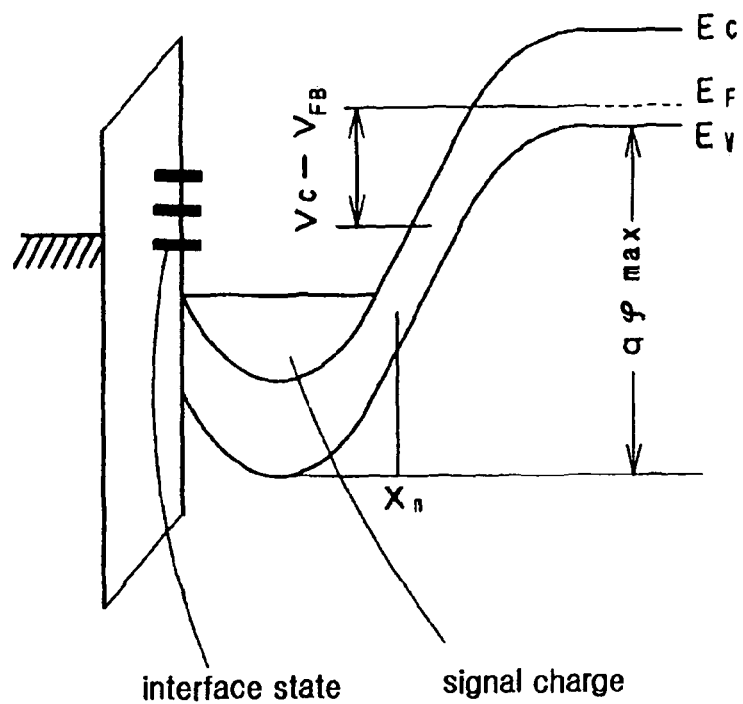

Step 1 shows a standby state. In this standby state, as explained in FIG. 8, the charge is remaining in the sensing part.

At step 3, the potential of the charge supply unit 1 is lowered, and the charge is supplied in the sensing part 3. And then, by raising the potential of the charge supply unit 1, the charge after being scooped by the charge supply unit 1 is left over in the sensing part 3 (step 5). At this time, if signal is not staying in the sensing part 3, as explained in FIG. 8, a signal is also remaining.

Consequently, by raising the potential of the elimination well 50 and increasing the depth of the elimination well 50, the charge remaining in the sensing part 3 is sucked into the elimination well 50. Since the substrate surface corresponding to the sensing part 3 is doped in the n type, the charge is not trapped on this surface. Therefore, the charge can be removed from the sensing part 3 in a short time.

When a signal is staying in the sensing part 3, it may be sucked in the elimination well 50, but since the quantity is always the same, no adverse effect is given to the output.

In this embodiment, in the standby state, the potential of the elimination electrode 62 is raised, and the potential of the elimination well 50 is set deeper than the potential of the sensing part 3, but it may be set at the same potential as the sensing part 3, and at step 6, the potential of this part may set deeper.

At step 7, the potential of the barrier 4 is raised, and the charge in the sensing par 3 is transferred to the floating diffusion part 5. At this time, in the sensing part 3, since charge due to the potential bump is not left over, the remaining charge is not accumulated in the floating diffusion part 5. Besides, since the substrate surface of the sensing part 3 is doped in the n type, charge is not trapped therein, and if a signal is staying, the whole amount of charge accumulated in the sensing part 3 can be transferred to the floating diffusion part 5 completely and in a short time.

At step 9, the potential of the elimination well 50 is returned to the standby state.

Figure 13:
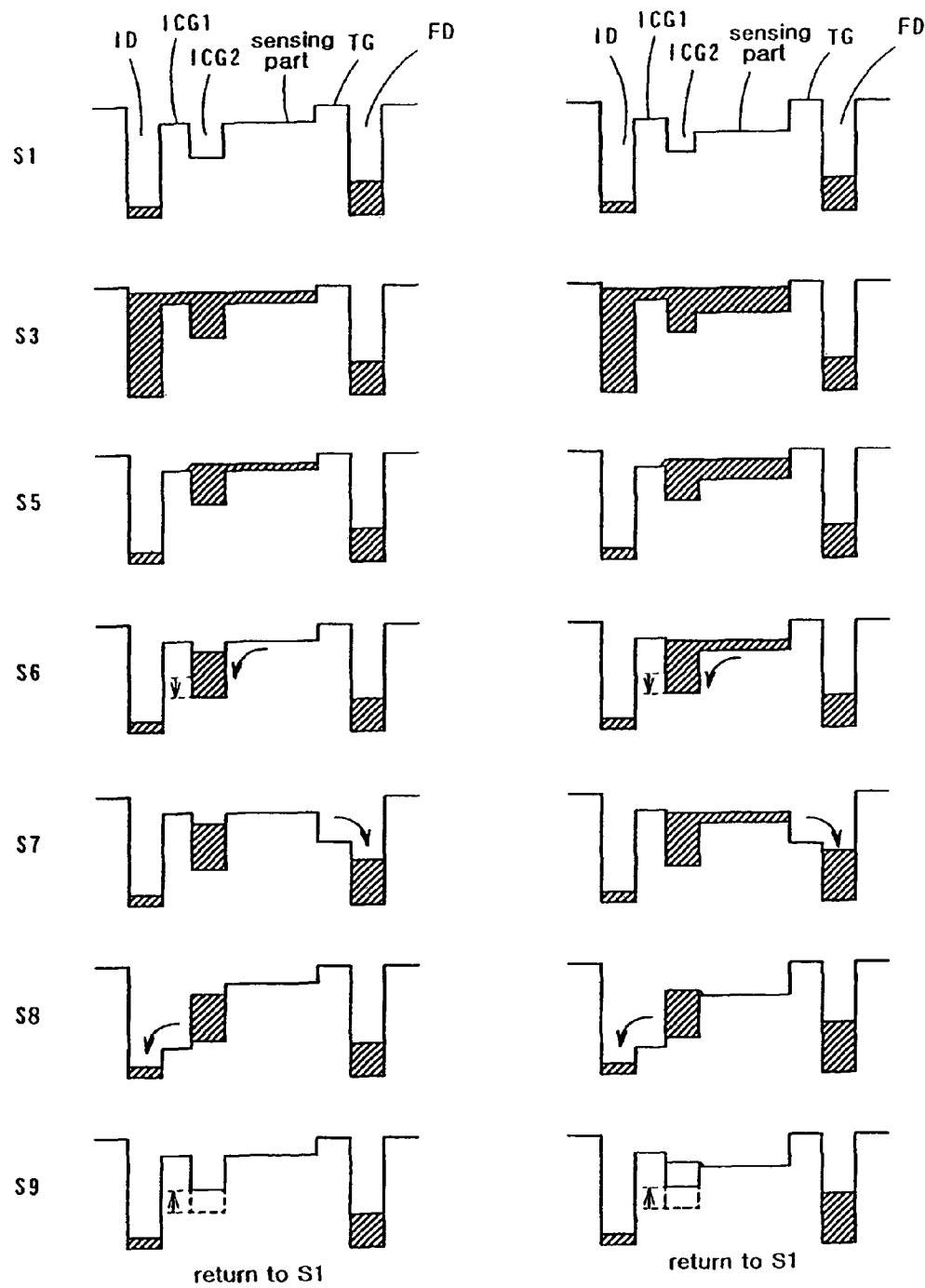
FIG. 13 shows other operation example of the charge accumulating type chemical and physical phenomenon detecting apparatus in an embodiment.

Prior to step 9, preferably, the charge accumulated in the elimination well 50 should be discharged. Accordingly, for example, at step 8 shown in FIG. 13, it is preferred to return the charge in the elimination well 50 to the charge supply unit 1 by raising the potential of the charge injection adjusting part 2.

Figure 14:
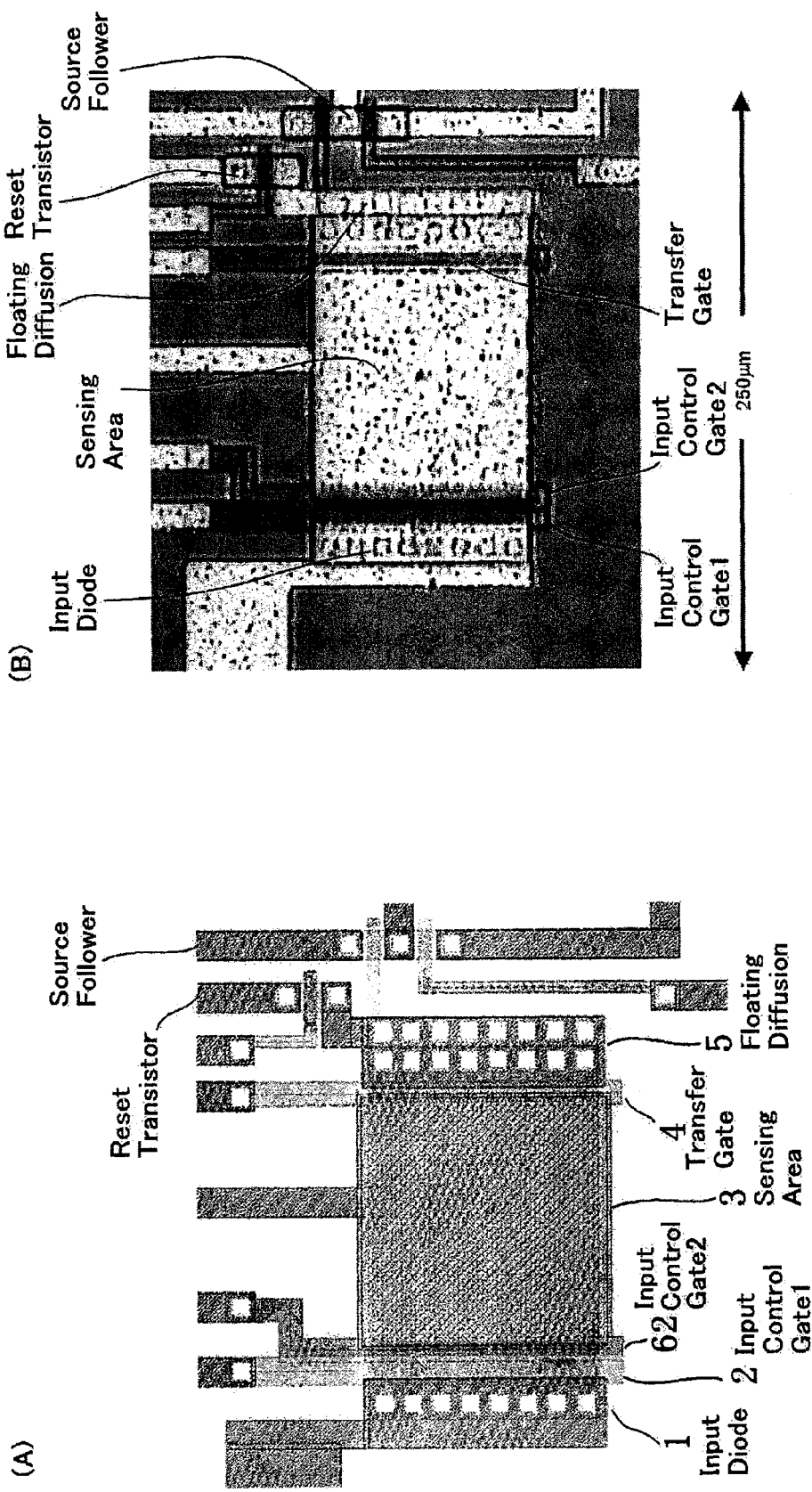
FIG. 14A shows a layout of elements of the charge accumulating type chemical and physical phenomenon detecting apparatus in an embodiment.
FIG. 14B is its plan view.

A layout of the apparatus in the embodiment is shown in FIG. 14A. Its microscopic image is shown in FIG. 14B.

The area of the sensing part 3 is 10000 $\mu m^2$, the area of the floating diffusion part 5 is 1500 $\mu m^2$. Film thickness of the silicon nitride film 23 as a cause of the potential bump is 0.1 $\mu m$.

Figure 15:
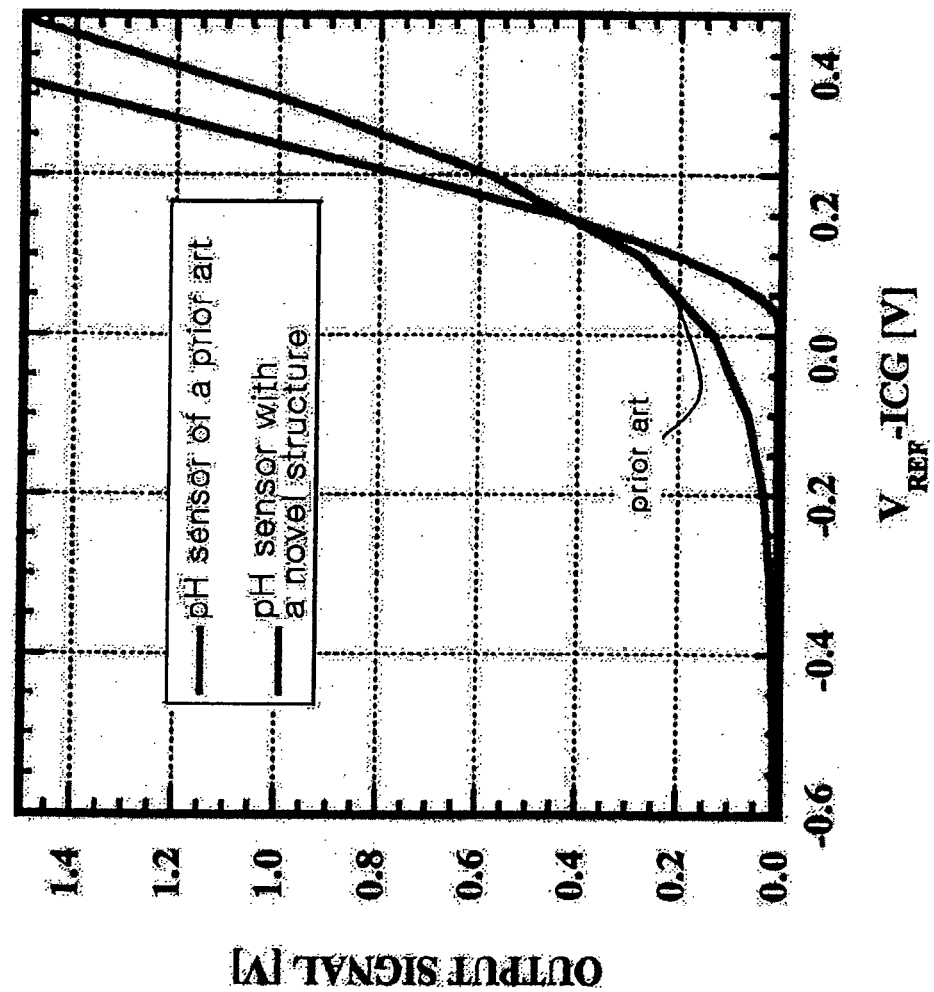
FIG. 15 shows an output characteristic of the charge accumulating type chemical and physical phenomenon detecting apparatus in an embodiment.

This apparatus was calibrated in pH standard solution 32. The output voltage when sweeping the reference voltage Vref is shown in FIG. 15. In the apparatus of prior art, a signal is issued even when the potential difference is zero (in a state not allowing a signal to stay) between the reference electrode 26 and the gate electrode 22. In the apparatus 60 of the embodiment, an ideal characteristic is shown.

A method of determining the pH from the characteristic shown in FIG. 15 is explained below.

Figure 16:
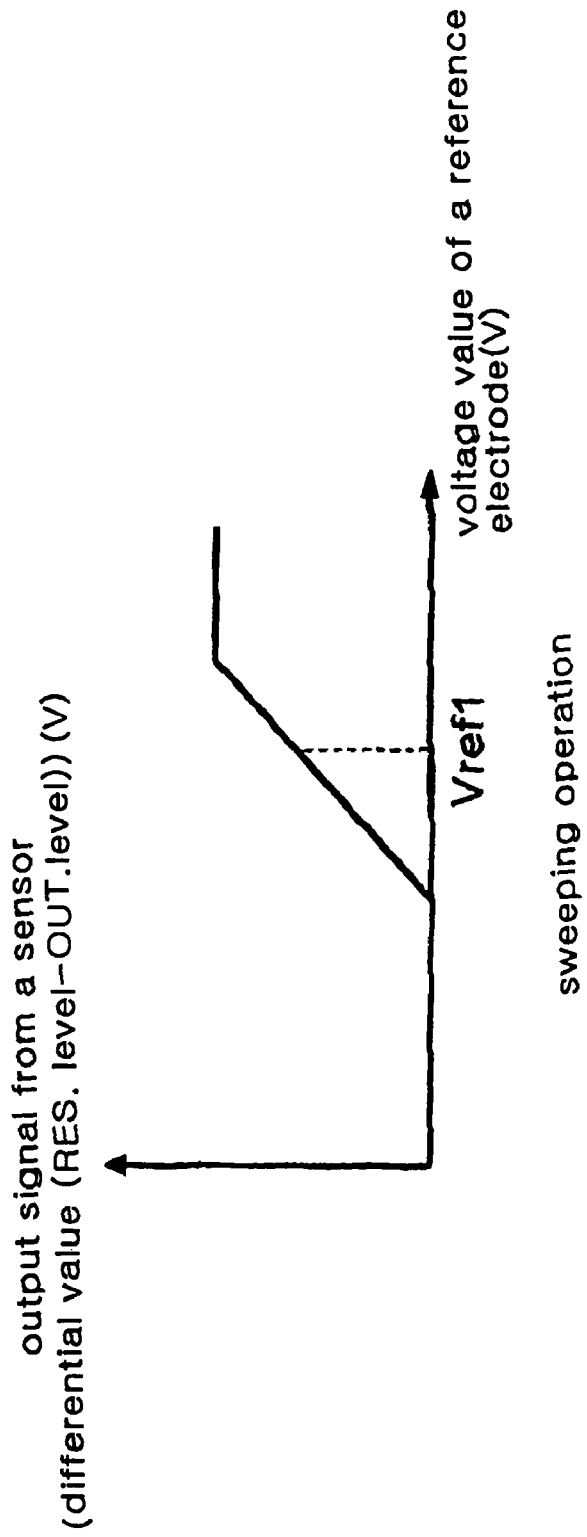
FIG. 16 is an explanatory diagram of a specifying method of a reference voltage Vref1.

A liquid cell 31 is filled with a solution of a specified pH (for example, standard solution of pH=7), and a relation of FIG. 16 is obtained by sweeping a reference voltage Vref. The cumulative degree of charge from the sensing part 3 to the floating diffusion part is 1.

In the graph obtained in FIG. 16, a reference voltage Vref1 in central portion of its gradient is specified. The reason of citing the reference voltage in a central portion of the gradient is because the values of pH before and after pH=7 can be measured widely by using the reference voltage Vref1. If the pH is never below 7 depending on the object of measurement, the reference voltage Vref can be set at a lower side of the gradient.

Figure 7:
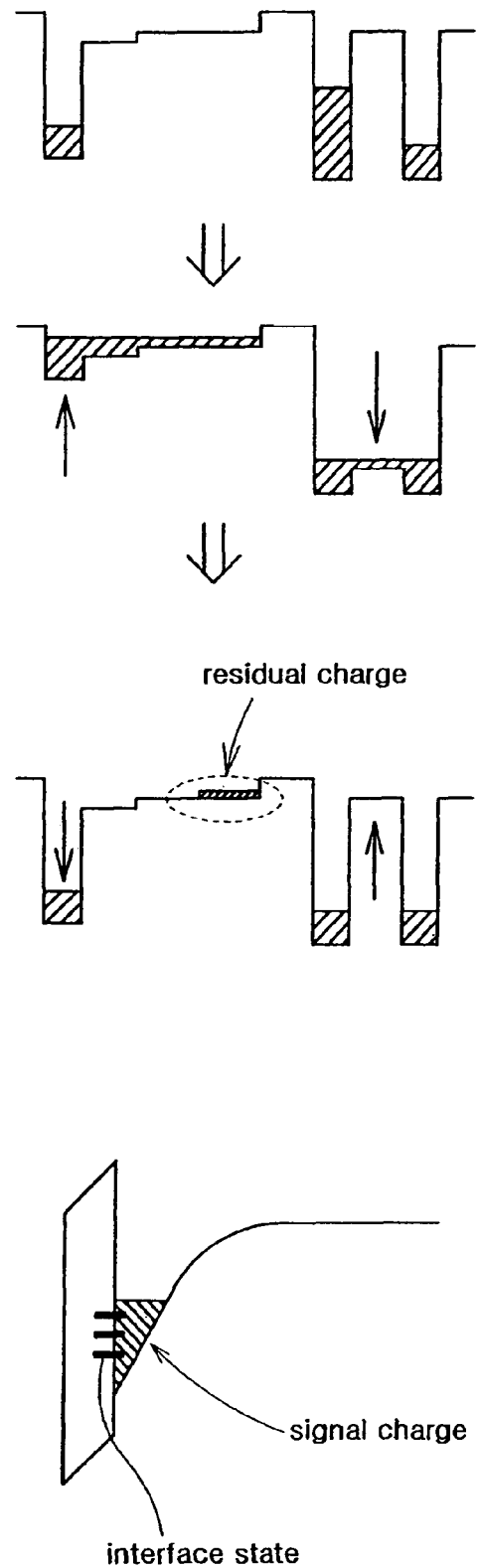
FIG. 7 is an explanatory diagram of effects of the charge trapped in a substrate surface of the sensing part.
Figure 17:
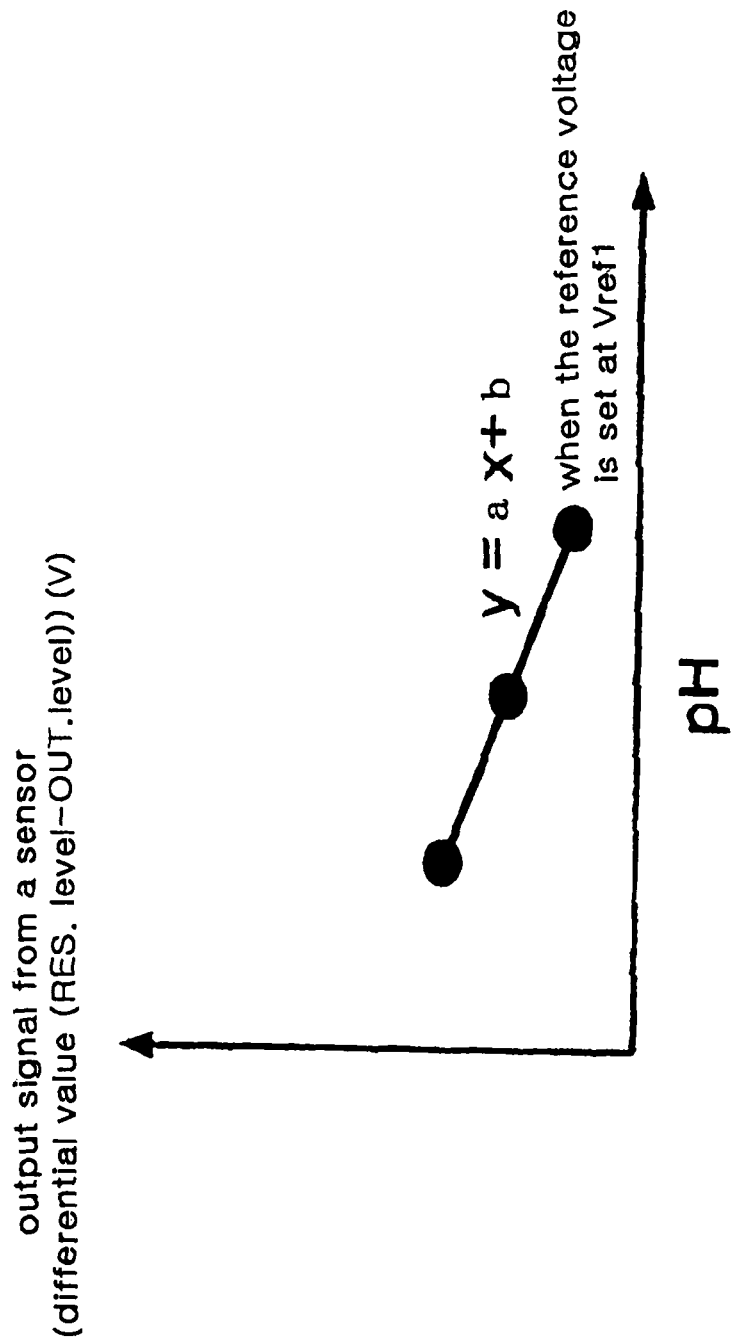
FIG. 17 shows the relation (calibration curve) of a pH value and an output voltage when the reference voltage is fixed at Vref1.

Next, the reference voltage is set at the specified Vref1, and different standard solutions are measured. In the example in FIG. 17, outputs of three standard solutions are determined (pH=4, 7, 9 from the left). From the results in FIG. 7, the relation of pH and an output signal is known to be expressed in the following linear function.

$$G(V)=F(x)=ax+b$$

where V is an output signal (voltage), in this case it is a differential value G (V) of a reset voltage and an output voltage. In other words, the differential value is expressed by the function G (V) of an output signal.

This linear function is a calibration curve for defining the relation of a pH value and an output value.

Therefore, it is known that the pH value can be specified from the output voltage V.

Figure 18:
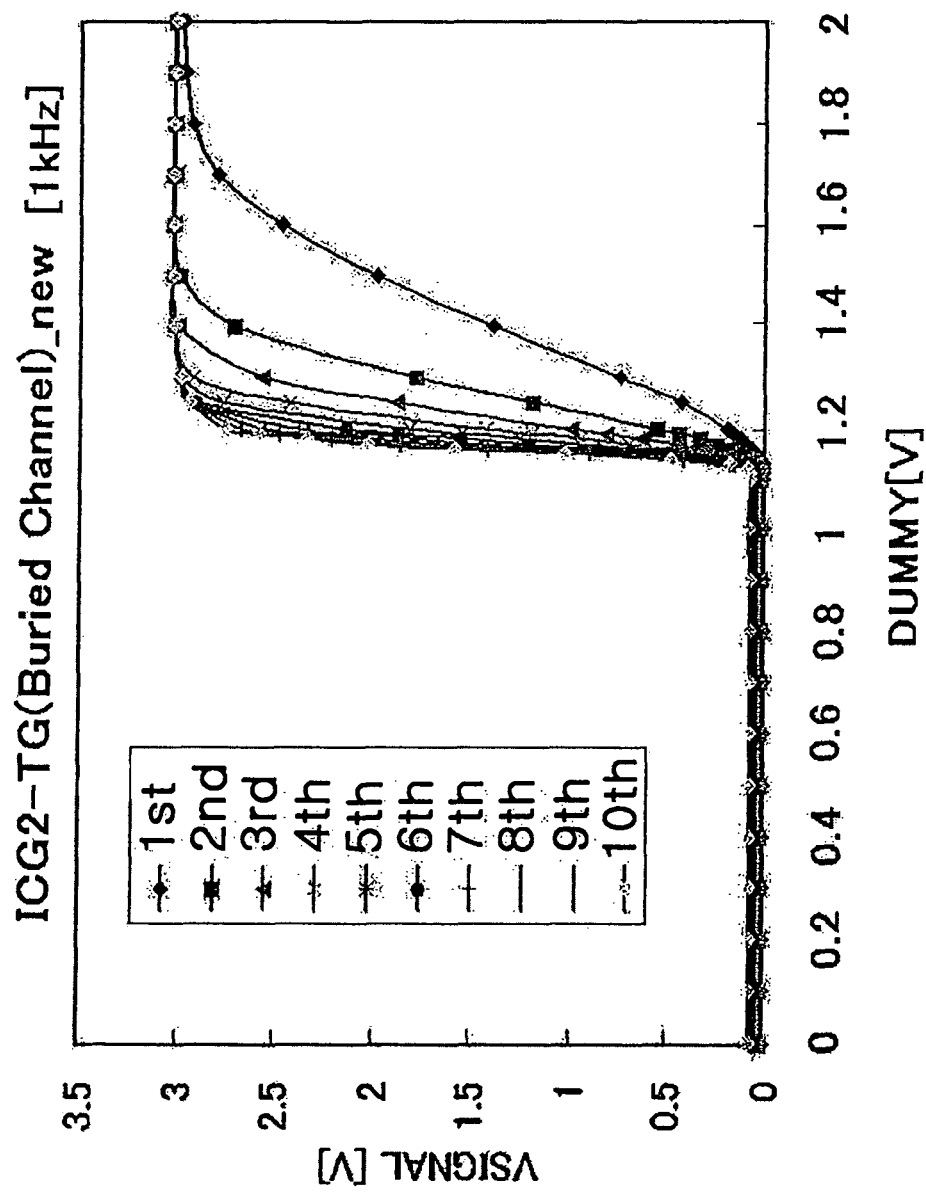
FIG. 18 shows a cumulative output characteristic of the charge accumulating type chemical and physical phenomenon detecting apparatus in an embodiment.
Figure 19:
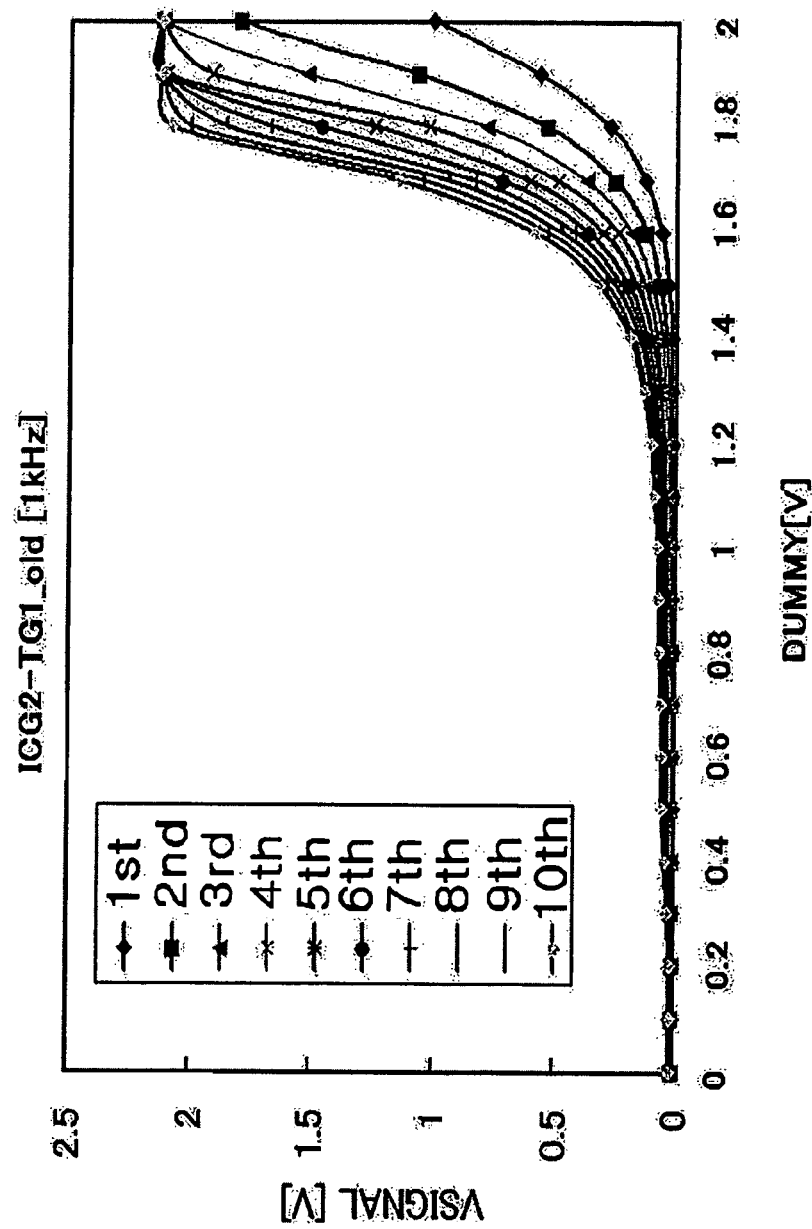
FIG. 19 shows a cumulative output characteristic of the charge accumulating type chemical and physical phenomenon detecting apparatus in a prior art.

FIG. 18 shows output changes by repetition of unit detection operations in the apparatus 60 of the embodiment. In FIG. 18, the axis of abscissas denotes the voltage value of reference electrode. In the standard solution (pH=7 in this example), by sweeping the reference voltage, pH changes can be created falsely. In the apparatus of the prior art, similarly, output changes by repetition of unit detection operations are shown in FIG. 19. By comparison of FIG. 18 and FIG. 19, in the apparatus of the embodiment, it is known that noise is not superposed when charges are accumulated on the floating diffusion part by repeating the unit detection operations. As a result, the sensitivity is enhanced. In this embodiment, by repeating the unit detection operation by 10 times, the sensitivity is enhanced by about 10 times.

Figure 20:
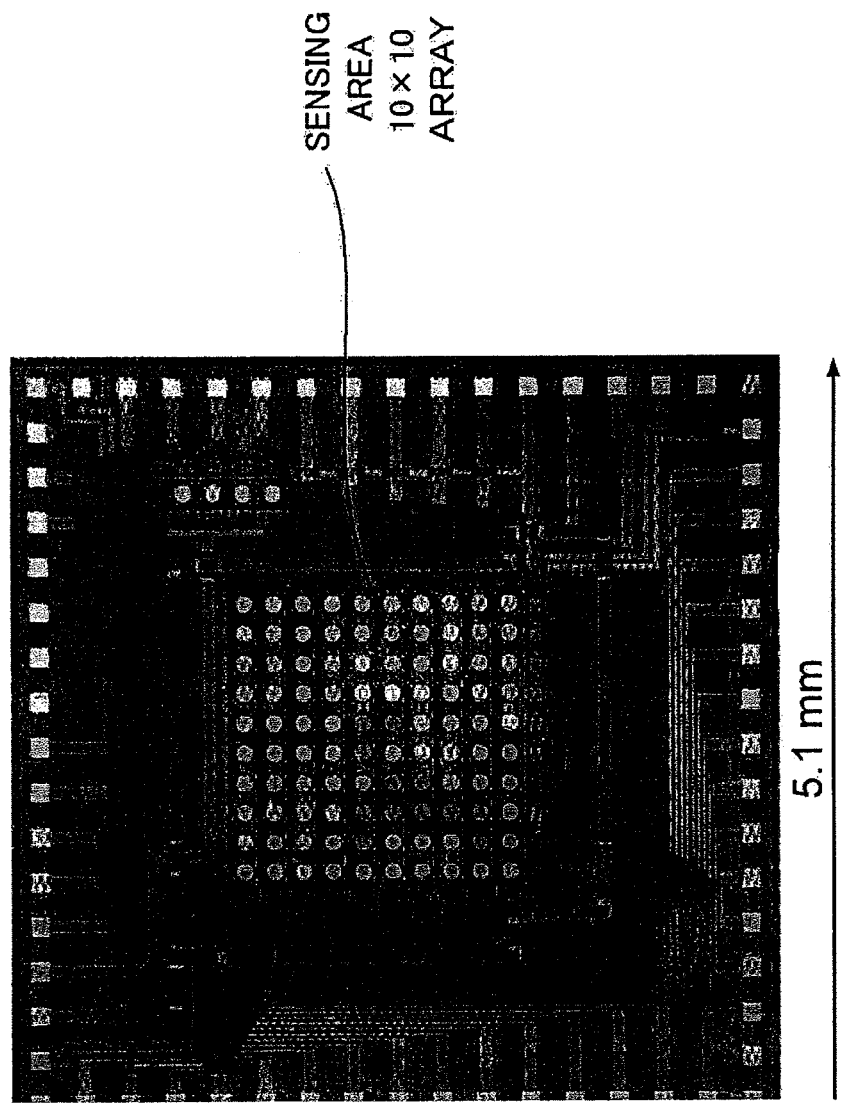
FIG. 20 is a plan view of arrayed sensor chips of the charge accumulating type chemical and physical phenomenon detecting apparatus in an embodiment.

FIG. 20 shows sensor chips including 10 vertical pieces and 10 lateral pieces of the apparatus shown in FIG. 11. Each apparatus is immersed in a same aqueous solution, and a signal from each apparatus is displayed as a color or pattern image corresponding to the magnitude of the signal.

Figure 21:
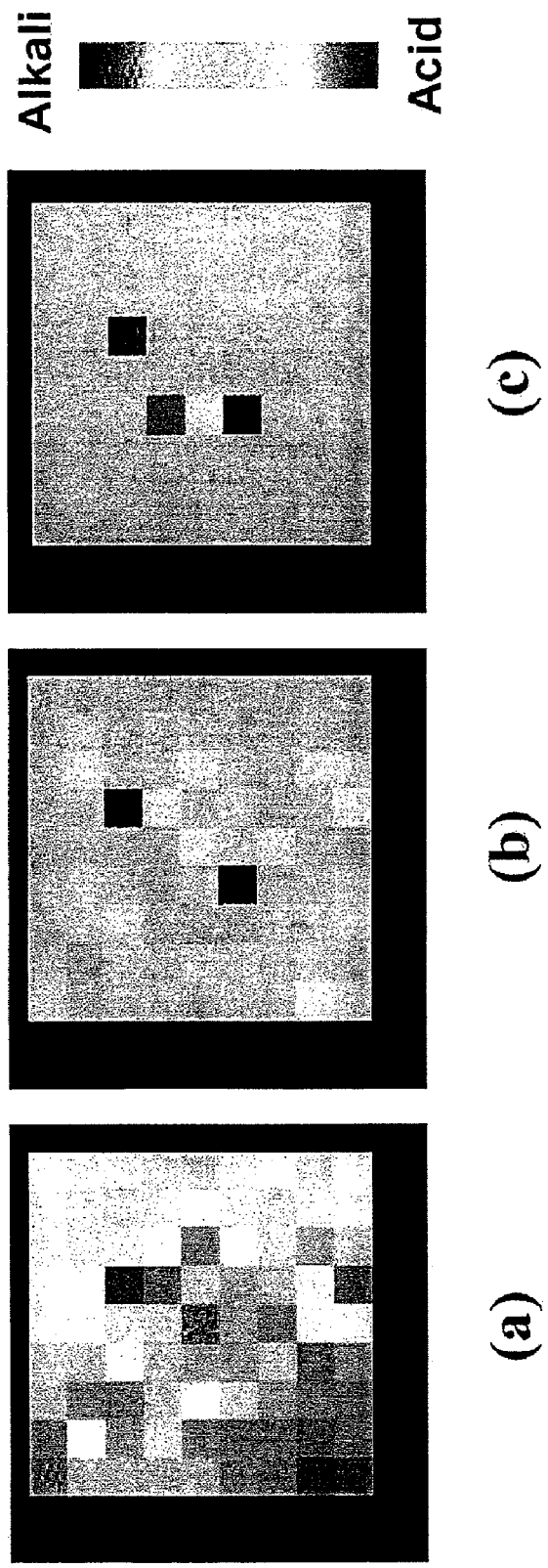
FIG. 21 is an output example of the same sensor chips.

FIG. 21 shows an example of an image display. The pixel for composing the image shown in FIG. 21 corresponds to each apparatus. FIG. 21(*a*) shows the initial acidic solution, and pH changes of entire solution after adding an alkaline solution to this acidic solution are shown in FIG. 21(*b*) and FIG. 21(*c*).

Figure 22:
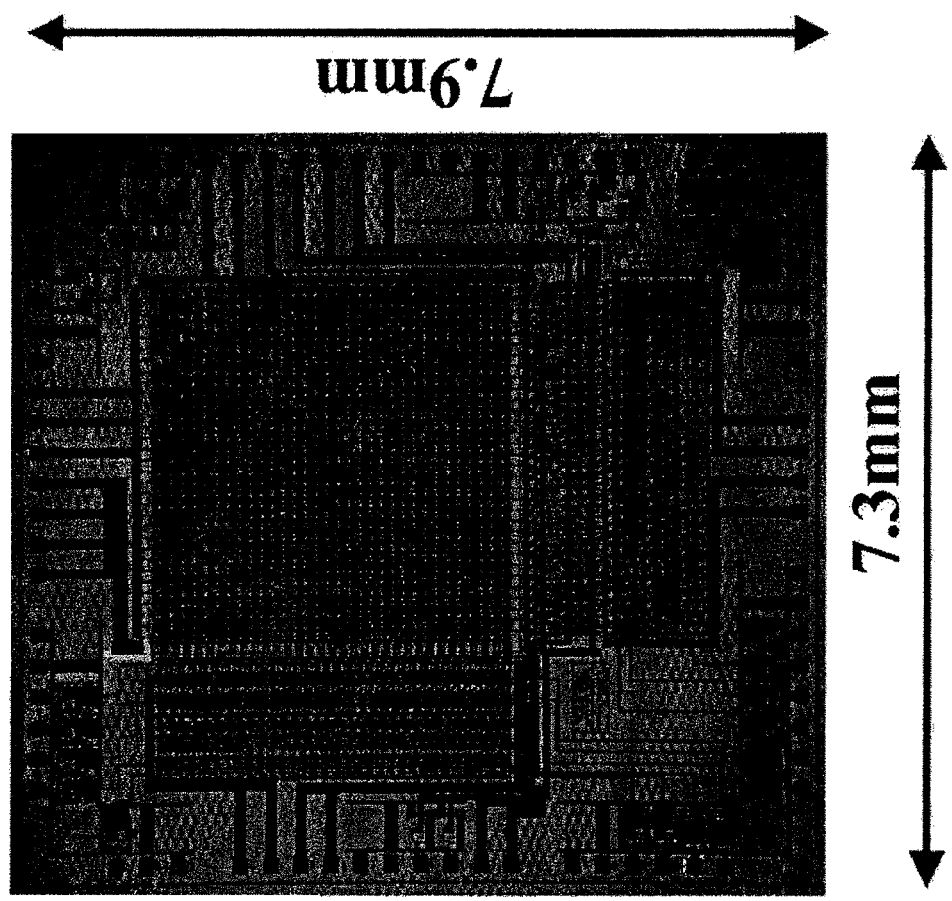
FIG. 22 shows other example of integrated sensor chips of the charge accumulating type chemical and physical phenomenon detecting apparatus in an embodiment.

FIG. 22 shows an array sensor consisting of 32 vertical pieces and 32 lateral pieces of the apparatus of the embodiment, and adding shift registers in the vertical and lateral directions.

In the detecting apparatus 60 of the embodiment, by using L-glutamate oxidase instead of the silicon nitride film, or laminating on the silicon nitride film, a chemical phenomenon detecting apparatus capable of detecting L-glutamic acid can be composed. Or by fixing DNA or antigen on the silicon nitride film, antigen or antibody of DNA can be detected. It is also possible to deposite a metal film and/or an SAM film (self-forming monomolecular film) on the silicon nitride film.

At the position of the silicon nitride film, by connecting the output of a temperature sensor, a pressure sensor, or a magnetic sensor, a physical phenomenon detecting apparatus capable of measuring the temperature, pressure, or magnetism can be realized.

The invention is not limited to the illustrated embodiment or example alone, but may be changed or modified freely within the scope easily devised by those skilled in the art without departing from the true spirit of the invention.

The invention claimed is:

1. A charge accumulating type chemical and physical phenomenon detecting apparatus comprising:
    a sensing part changed in potential depending on a chemical or physical phenomenon,
    a charge supply unit for supplying a charge to the sensing part,
    a charge injection adjusting part interposed between the sensing part and the charge supply unit, and
    a floating diffusion part for accumulating the charge transferred from the sensing part,
    wherein the charge in the sensing part by a potential bump formed between the charge injection adjusting part and the sensing part is scooped by lowering the potential of the charge supply unit, and raising the potential of the charge supply unit from the state of supplying charge into the sensing part, and the charge remaining in the sensing part is discharged to an elimination well formed consecutively to the sensing part.

2. The apparatus according to claim 1, wherein a depth of a potential well of the elimination well is varied.

3. The apparatus according to claim 2, wherein the elimination well has a depth of first potential well when supplying a charge from the charge supply unit to the sensing part, and has a depth of a second potential well before transferring the charge from the sensing part to the floating diffusion part, and the depth of the second potential well is deeper than the depth of the first potential well.

4. The apparatus according to claim 1, further comprising a means for returning the charge accumulated in the elimination well into the charge supply unit.

5. The apparatus according to claim 1, wherein the charge existing in the sensing part is positioned apart from a surface of a substrate.

6. The apparatus according to claim 5, wherein the substrate comprises a first region corresponding to at least the sensing part and doped with an impurity of a first conductive type, and a second region disposed in the surface of the substrate and doped with an impurity of a second conductive type different from the first conductive type and the charge is positioned within the second region.

7. The charge accumulating type chemical and physical phenomenon detecting apparatus according to claim 1, wherein a first charge control electrode corresponding to the charge injection adjusting part and a second charge control electrode controlling the potential of the elimination well are provided between the charge supply unit and the sensing part, and the first charge control electrode and the second charge control electrode are controlled independently.

8. A charge accumulating type chemical and physical phenomenon detecting apparatus, comprising:
a sensing part disposed within a substrate for detecting an ion signal, and
a first charge control electrode and a second charge control electrode are provided between the sensing part and a charge supply unit, and controlled independently,
wherein the substrate comprises a first region corresponding to at least the sensing part and doped with an impurity of a first conductive type, and a second region disposed in a surface of the substrate and doped with an impurity of a second conductive type different from the first conductive type, and a charge is positioned within the second region.

* * * * *